(12) United States Patent
Wayte

(10) Patent No.: US 7,097,783 B2
(45) Date of Patent: Aug. 29, 2006

(54) METHOD FOR INSPECTING A TITANIUM-BASED COMPONENT

(75) Inventor: Peter Wayte, Maineville, OH (US)

(73) Assignee: General Electric Company, Schenectady, NY (US)

( * ) Notice: Subject to any disclaimer, the term of this patent is extended or adjusted under 35 U.S.C. 154(b) by 189 days.

(21) Appl. No.: 10/622,304

(22) Filed: Jul. 17, 2003

(65) Prior Publication Data

US 2005/0011863 A1    Jan. 20, 2005

(51) Int. Cl.
*C23F 1/00* (2006.01)

(52) U.S. Cl. .................. 216/84; 216/83; 216/96; 216/100; 216/109; 252/79.1; 252/79.2; 252/79.3

(58) Field of Classification Search .......... 216/83, 216/84, 100, 109, 96; 252/79.1, 79.2, 79.3
See application file for complete search history.

(56) References Cited

U.S. PATENT DOCUMENTS

| | | | |
|---|---|---|---|
| 3,850,712 A * | 11/1974 | Broughton et al. ......... 216/109 |
| 4,063,644 A | 12/1977 | Hoffman et al. ......... 209/111.6 |
| 4,318,792 A | 3/1982 | Snow ..................... 204/181 R |
| 5,209,829 A | 5/1993 | Gondel et al. .......... 204/129.75 |
| 5,227,035 A | 7/1993 | Briot et al. ............ 204/129.75 |
| 5,484,665 A | 1/1996 | Singh et al. ................ 428/661 |
| 5,705,082 A * | 1/1998 | Hinson ....................... 216/95 |
| 5,853,561 A | 12/1998 | Banks ........................ 205/646 |
| 5,976,695 A | 11/1999 | Hajmrle et al. ............. 428/402 |
| 6,401,537 B1 | 6/2002 | Gigliotti, Jr. et al. ........ 73/598 |

* cited by examiner

*Primary Examiner*—Shamim Ahmed
(74) *Attorney, Agent, or Firm*—Harrington & Smith, LLP

(57) ABSTRACT

A process for detecting an aluminum-based material deposited onto a titanium-based gas turbine engine component during engine operation is disclosed. The process comprises immersing at least a portion of the titanium-based component, which has been subjected to engine operation, into an acid solution to form an etched component. The acid solution comprises sodium fluoride, sulphuric acid and water. The etched component may then be removed from the solution and visually inspected for dark areas in contrast to light areas, the dark areas indicating deposited aluminum-based material.

26 Claims, 1 Drawing Sheet

METHOD FOR INSPECTING A TITANIUM-BASED COMPONENT

FIELD OF THE INVENTION

The present invention generally relates to methods for inspecting titanium-based components, such as the components of a gas turbine engine, after engine operation. More particularly, this invention relates to an inspection method for detecting the presence of aluminum-based material deposited on titanium-based gas turbine engine components.

BACKGROUND OF THE INVENTION

Titanium-based materials are useful because of their relatively low weight and high strength over a wide range of operating temperatures. Titanium or titanium alloys often are the material of choice for high performance gas turbine engine components, such as the fan rotor, fan blades, compressor disk and compressor blades. A wide range of titanium alloys are available, each of which confer a particular combination of characteristics to the component. For example, some gas turbine compressor blades are made of the commercially available Ti-6A1-4V alloy.

The efficiency of gas turbine engines is dependent, in part, on the ability of the above titanium-based and other engine components to combine air and products of combustion, to intended pathways. Leakage from such design flowpaths can reduce engine performance and efficiency and thus gas turbine engine designers have developed a variety of sealing arrangements, such as abradable seals, to work in conjunction with other components to reduce or control leakage. For example, abradable seals are used on the shrouds of compressors to insure efficient operation of the engine by minimizing gas leakage in the compressor and turbine sections. Although the engine is typically designed and manufactured to precise dimensional tolerances, centrifugal and thermal expansion of the rotating and stationary members makes it difficult to achieve zero clearances. Thus, abradable seals often are employed on surfaces of the stationary member allowing penetration of rotating blades into the seal.

Some modern gas turbine engines employ titanium alloy rotor blades and an AlSi coated seal. During operation, the titanium alloy blades may contact and rub into casings or adjacent hardware coated with AlSi. The condition of the blade after operation can vary depending on the severity of the rub. Severe rubs may result in over heating of the blade tip with a range of conditions varying from an associated color tint on the tip, transformation of the blade tip microstructure to deformation of the blade tip. However, there are no visual indications for blades that experienced mild contact into the AlSi coating resulting in the deposit of aluminum on the blade. Such deposit onto the blades is aerodynamically undesirable and may result in decreased engine performance and efficiency. Thus, if a blade rub is suspected, all of the blades are removed from the engine and replaced.

Accordingly, there exists a need for a nondestructive inspection technique that identifies the presence of aluminum-based material deposited on titanium-based components during engine operation. The present invention satisfies this need.

BRIEF DESCRIPTION OF THE INVENTION

In one embodiment of the invention, a process for detecting an aluminum-based material deposited onto a titanium-based gas turbine engine component during engine operation is disclosed. The process comprises immersing at least a portion of the titanium-based component, which has been subjected to engine operation, into an acid solution to form an etched component, wherein the acid solution comprises sodium fluoride, sulphuric acid and water. The process further comprises removing the etched component from the solution and visually inspecting the etched component for dark areas in contrast to light areas, the dark areas indicating deposited aluminum-based material.

In another embodiment of the invention, a process for detecting an aluminum-based material deposited onto a titanium-based gas turbine engine component during engine operation, comprises immersing, for between about 45 seconds and about 3 minutes, at least a portion of the titanium-based component, which has been subjected to engine operation, into an acid solution to form an etched component. The acid solution comprises, per liter: i) about 15 g/liter of sodium fluoride; ii) about 75 g/liter of sulphuric acid having a density of about 1.84; and iii) balance water. The process further comprises removing the etched component from the solution; washing the etched component in water, followed by drying; and visually inspecting the etched component under magnified conditions for dark areas in contrast to light areas, the dark areas indicating deposited aluminum-based material.

In accordance with a further embodiment, a process for detecting an aluminum-based material deposited onto a titanium-based gas turbine engine component during engine operation comprises swab etching at least a portion of the titanium-based component, which has been subjected to engine operation, with an acid solution to form an etched component, the acid solution comprising i) sodium fluoride, ii) sulphuric acid and iii) water. The process further comprises visually inspecting the etched component for dark areas in contrast to light areas, the dark areas indicating deposited aluminum-based material.

In accordance with further embodiments of the invention, calcium fluoride, potassium fluoride or hydrofluoric acid may be substituted for the sodium fluoride constituent.

DETAILED DESCRIPTION OF THE INVENTION

Figure 1:
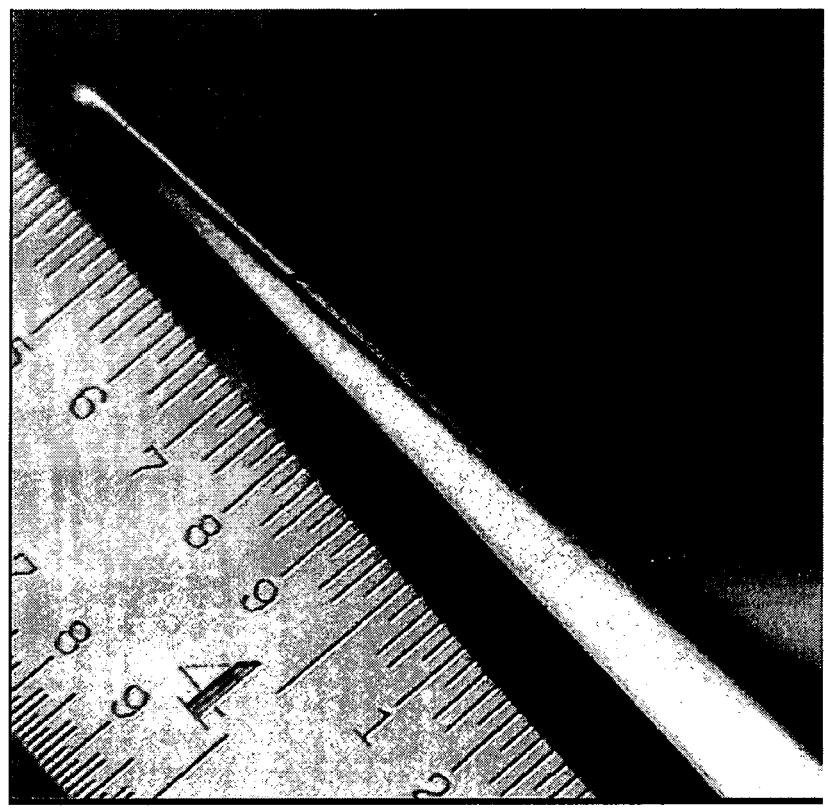
FIG. 1 shows, at about 5× magnification, the condition of a blade that has experienced tip rub with an AlSi coating during engine operation.

The present invention is useful in the inspection of titanium-based gas turbine engine components subjected to engine operation. As used herein, the term "titanium-based" includes titanium alloys, as well as substantially pure titanium. The following description is provided with reference to gas turbine engine components, particularly blades, but it will be understood that the present invention also is applicable to any titanium-based substrate which may have contacted an aluminum-based material. As also used herein, the term "aluminum-based" includes substantially pure aluminum, as well as aluminum in combination with other substances.

In accordance with one embodiment of the present invention, a titanium-based blade, which has been subjected to engine service, is inspected to determine if an aluminum-based material has been deposited onto the component. Such aluminum deposit may occur as a result of the blade tip contacting an aluminum-based coating, such as an AlSi coating, of an abradable seal during a rub. An aluminum deposit also may result from contact with aluminum-based hardware, such as a shroud.

The blade may be removed from the engine for inspection and rinsed with water prior to inspection. According to one aspect of the invention, at least a portion of the blade requiring inspection, such as the blade tip, is immersed in an acid solution. Alternatively, an entire component may be immersed, if desired.

The acid solution may comprise sodium fluoride, sulphuric acid and water. In one embodiment, the solution comprises, per liter, about 5 to about 50 g sodium fluoride, about 50 to about 100 g sulphuric acid, balance water. The duration of the immersion time is dependent upon the concentration of the solution. For example, with respect to the above, at least a portion of the blade may be immersed in the solution for between about 1 and about 5 minutes (for about 5 g sodium fluoride) and about 25 seconds to about 1 minute (for about 50 g sodium fluoride). Preferably, the solution comprises, per liter, about 15 g sodium fluoride, about 75 g sulphuric acid having a density of about 1.84, balance water, and the component is immersed in the solution for between about 45 seconds and about 3 minutes. All subranges therebetween also are included in the present invention.

Alternatively, potassium fluoride, calcium fluoride or hydrofluoric acid may be substituted for the sodium fluoride constituent, in the amounts described above for the sodium fluoride. However, longer immersion times, such as about 4× or greater than the above described times, may be required if potassium fluoride or calcium fluoride is employed. If hydrofluoric acid is substituted for the sodium fluoride constituent, shorter immersion times, such as about ½× or less than the above described immersion times for sodium fluoride may be employed. However, use of hydrofluoric acid may have secondary effects on the exposed component.

The acid solution composition is particularly effective at normal temperatures between about 15° C. and about 25° C. The solution also may be agitated prior to and during immersion. If desired, the solution may be recharged or replenished during use by adding further suitable amounts of the solution constituents, particularly sodium fluoride, to maintain desired etching duration times.

Figure 2:
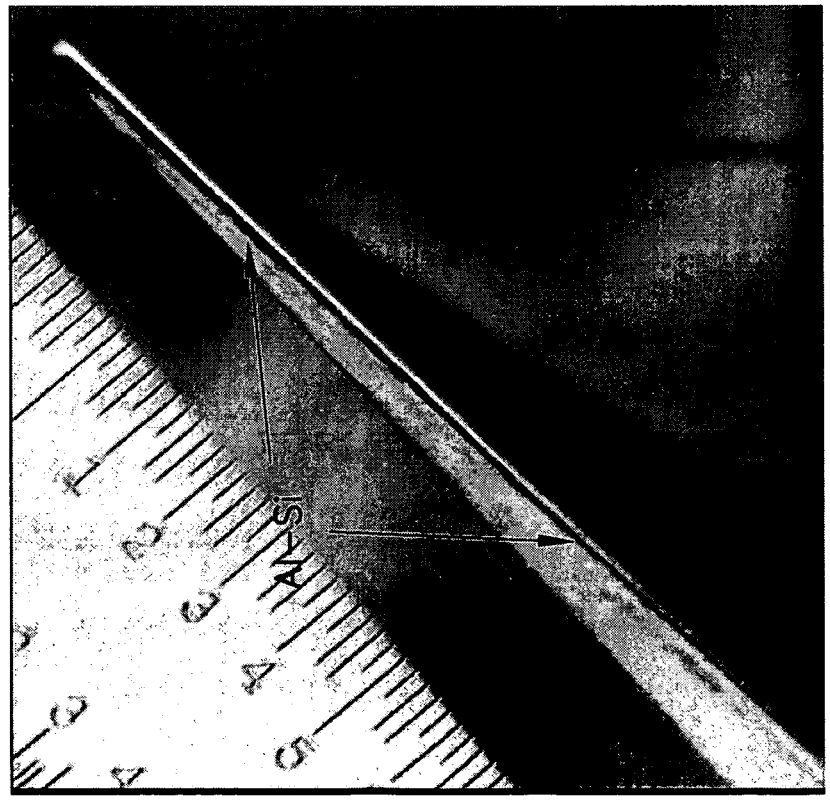
FIG. 2 shows, at about 5× magnification, the condition of another blade that has experienced tip rub with an AlSi coating during engine operation.

After immersion, the blade may be removed from the solution, washed with water and air dried. The blade then may be visually inspected for the appearance of dark areas, which indicate rubbed surfaces or surfaces of the blades exposed to an aluminum-based material, such as AlSi coating. These dark areas are in contrast to the areas of lighter appearance on the blade, which indicate non-rubbed areas or areas of the blade that have not contacted the aluminum-based material. The dark areas of contact may appear as black lines on the blades. Visual inspection at a magnification of about 4× to about 25×, preferably about 10×, is particularly useful for inspection. Referring to FIGS. 1 and 2, shown are tips of two titanium alloy blades which have contacted an AlSi seal coating during engine operation. Upon application of the preferred process of the present invention, a black line (indicated by arrows on FIGS. 1 and 2 at about 5× magnification) was visible on each blade. Advantageously, if such a contrasting dark area is not shown on the blade, the blade may be returned to operation and not unnecessarily scrapped.

Alternatively, it may not be necessary to remove the blade from the engine prior to application of solution. For example, a "swab etch" method may be employed by repeatedly applying the afore-described solution onto the blade with a saturated cloth, cotton wool material or other suitable applicator so that the blade may be exposed to the solution for a suitable time, such as the duration comparable to that of the immersion method. The blade then may be washed with water, which can be applied with the use of any suitable applicator such as a cloth or spray device, and dried.

An advantage of the present invention is providing a nondestructive inspection technique that comprises minimal steps and is cost effective to implement. The inspection may be set up easily and inexpensively, without the need for special, complicated equipment. Moreover, operators also may be readily trained in the inspection process.

Another advantage of the present invention is that the process removes less than 0.0001 inches (2.564 μm) from the surface of the component. Thus, the components will meet dimensional requirements after inspection and non-rubbed components may be readily returned to service.

A further advantage of the present invention is that it employs an uncomplicated etch immersion or swab etch technique, which may readily and quickly reveal component rub or exposure to an aluminum-based material without the requirement of further processing of the part for inspection.

While various embodiments are described herein, it will be appreciated from the specification that various combinations of elements, variations or improvements therein may be made by those skilled in the art, and are within the scope of the invention.

What is claimed is:

1. A process for detecting an aluminum-based material deposited onto a titanium-based gas turbine engine component during engine operation when there is not a visual indication of at least a portion of the aluminum-based material on the component, consisting of the sequential steps of:
   immersing at least a portion of the titanium-based component, which has been subjected to engine operation, into an acid solution to form an etched component, the acid solution comprising sodium fluoride, sulphuric acid and water;
   removing the etched component from the solution; and
   visually inspecting the etched component for dark areas in contrast to light areas, the dark areas indicating deposited aluminum-based material.

2. The process of claim 1, wherein the titanium-based component is a titanium alloy blade.

3. The process of claim 1, wherein at least a portion of the component is immersed in an acid solution comprising, per liter i) about 15 g/liter of sodium fluoride; ii) about 75 g/liter of sulphuric acid having a density of about 1.84; and iii) balance water, for between about 45 seconds and about 3 minutes.

4. The process of claim 2, wherein only a blade tip is immersed in the solution.

5. The process of claim 1, wherein the entire component is immersed in the solution.

6. The process of claim 1, wherein the etched component is visually inspected at a magnification of about 4× to about 25×.

7. The process of claim 6, wherein the etched component is visually inspected at a magnification of about 10×.

8. The process of claim 1, wherein at least a portion of the component is immersed in an acid solution comprising, per liter i) about 5 to about 50 g/liter of sodium fluoride; ii) about 50 to about 100 g/liter of sulphuric acid having a density of about 1.84; and iii) balance water.

9. The process of claim 8, wherein the at least a portion of the component is immersed in the solution from between about 1 minute and about 5 minutes.

10. The process of claim 8, wherein the at least a portion of the component is immersed in the solution from about between about 25 seconds and about 1 minute.

11. The process of claim 1, wherein the aluminum-based material is AlSi.

12. A process for detecting an aluminum-based material deposited onto a titanium-based gas turbine engine component during engine operation when there is not a visual indication of at least a portion of the aluminum-based material on the component, consisting of the sequential steps of:
   immersing, for between about 45 seconds and about 3 minutes, at least a portion of the titanium-based component, which has been subjected to engine operation, into an acid solution to form an etched component, the acid solution comprising, per liter:
      i) about 15 g/liter of sodium fluoride;
      ii) about 75 g/liter of sulphuric acid having a density of about 1.84; and
      iii) balance water;
   removing the etched component from the solution;
   washing the etched component in water, followed by drying; and
   visually inspecting the etched component under magnified conditions for dark areas in contrast to light areas, the dark areas indicating deposited aluminum-based material.

13. The process of claim 12, wherein the titanium-based component is a titanium alloy blade.

14. The process of claim 13, wherein only a blade tip is immersed in the solution.

15. The process of claim 12, wherein the entire component is immersed in the solution.

16. The process of claim 12, wherein the etched component is visually inspected at a magnification of about 4× to about 25×.

17. The process of claim 16, wherein the etched component is visually inspected at a magnification of about 10×.

18. The process of claim 12, wherein the aluminum-based material is AlSi.

19. A process for detecting an aluminum-based material deposited onto a titanium-based gas turbine engine component during engine operation when there is not a visual indication of at least a portion of the aluminum-based material on the component, consisting of the sequential steps of:
   swab etching at least a portion of the titanium-based component, which has been subjected to engine operation, with an acid solution to form an etched component, the acid solution comprising sodium fluoride, sulphuric acid and water; and
   visually inspecting the etched component for dark areas in contrast to light areas, the dark areas indicating deposited aluminum-based material.

20. The process of claim 19, wherein the swab etching step comprises saturating an applicator with the acid solution and repeatedly applying the acid solution to at least a portion of the titanium-based component.

21. The process of claim 20, wherein the applicator is selected from the group consisting of a cloth, a cotton wool material and spray device.

22. A process for detecting an aluminum-based material deposited onto a titanium-based gas turbine engine component during engine operation when there is not a visual indication of at least a portion of the aluminum-based material on the component, consisting of the sequential steps of:
   immersing at least a portion of the titanium-based component, which has been subjected to engine operation, into an acid solution to form an etched component, the acid solution comprising i) calcium fluoride, potassium fluoride or hydrofluoric acid, ii) sulphuric acid and iii) water;
   removing the etched component from the solution; and
   visually inspecting the etched component for dark areas in contrast to light areas, the dark areas indicating deposited aluminum-based material.

23. A process for detecting an aluminum-based material deposited onto a titanium-based gas turbine engine component during engine operation when there is not a visual indication of at least a portion of the aluminum-based material on the component, consisting of the sequential steps of:
   swab etching at least a portion of the titanium-based component, which has been subjected to engine operation, with an acid solution to form an etched component, the acid solution comprising i) calcium fluoride, potassium fluoride or hydrofluoric acid, ii) sulphuric acid and iii) water; and
   visually inspecting the etched component for dark areas in contrast to light areas, the dark areas indicating deposited aluminum-based material.

24. The process of claim 1, wherein the component is rinsed with water after removing the component from the solution and prior to visually inspecting the etched component.

25. The process of claim 22, wherein the solution comprises i) calcium fluoride or potassium fluoride ii) sulphuric acid and iii) water.

26. The process of claim 23, wherein the solution comprises i) calcium fluoride or potassium fluoride ii) sulphuric acid and iii) water.

* * * * *